(12) United States Patent
Zeman et al.

(10) Patent No.: US 8,926,717 B2
(45) Date of Patent: Jan. 6, 2015

(54) METHODS AND SYSTEMS FOR PRODUCING SYNTHETIC FUEL

(75) Inventors: Frank S. Zeman, Brooklyn, NY (US); Marco J. Castaldi, Yonkers, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 728 days.

(21) Appl. No.: 12/663,295

(22) PCT Filed: Jul. 28, 2008

(86) PCT No.: PCT/US2008/071314
§ 371 (c)(1), (2), (4) Date: Jun. 2, 2010

(87) PCT Pub. No.: WO2009/018200
PCT Pub. Date: Feb. 5, 2009

(65) Prior Publication Data
US 2010/0293845 A1 Nov. 25, 2010

Related U.S. Application Data

(60) Provisional application No. 60/952,385, filed on Jul. 27, 2007, provisional application No. 60/985,401, filed on Nov. 5, 2007.

(51) Int. Cl.
*C10L 1/18* (2006.01)
*C07C 29/151* (2006.01)
*C01B 3/34* (2006.01)

(52) U.S. Cl.
CPC ............... *C07C 29/1518* (2013.01); *C01B 3/34* (2013.01); *C01B 2203/0238* (2013.01); *C01B 2203/061* (2013.01); *C01B 2203/062* (2013.01); *C01B 2203/1241* (2013.01)

USPC ............................................ 44/451; 518/702

(58) Field of Classification Search
USPC ........................................................... 44/451
See application file for complete search history.

(56) References Cited

U.S. PATENT DOCUMENTS

| | | | | |
|---|---|---|---|---|
| 1,609,593 A | * | 12/1926 | Woodruff et al. | 518/717 |
| 1,741,308 A | * | 12/1929 | Jaeger | 518/706 |
| 1,824,896 A | * | 9/1931 | Jaeger | 518/713 |
| 4,348,486 A | * | 9/1982 | Calvin et al. | 518/704 |
| 4,348,487 A | | 9/1982 | Goldstein et al. | |
| 2003/0099594 A1 | | 5/2003 | Lyon | |

OTHER PUBLICATIONS

International Search Report and the Written Opinion of the International Searching Authority, International Application No. PCT/US2008/071314, filed Jul. 28, 2008.

* cited by examiner

*Primary Examiner* — Cephia D Toomer
(74) *Attorney, Agent, or Firm* — Wiggin and Dana LLP; Anthony P. Gangemi

(57) ABSTRACT

Methods and systems for producing a synthetic fuel are disclosed. In some embodiments, the methods and systems include the following: thermally reforming methane and carbon dioxide to generate a syngas including a first quantity of carbon monoxide and a first quantity of hydrogen; oxidizing the quantity of first carbon monoxide with a metal to produce metal oxide and carbon thereby separating oxygen from the carbon monoxide; gasifying the carbon using steam to produce a second quantity of carbon monoxide and a second quantity of hydrogen; reacting the metal oxide with methane to produce metal oxide, carbon dioxide, and a third quantity of hydrogen; and synthesizing the first quantity of carbon monoxide, the first quantity of hydrogen, the second quantity of hydrogen, and the third quantity of hydrogen to form the synthetic fuel.

6 Claims, 2 Drawing Sheets

METHODS AND SYSTEMS FOR PRODUCING SYNTHETIC FUEL

CROSS REFERENCE TO RELATED APPLICATION(S)

This application claims the benefit of U.S. Provisional Application Nos. 60/952,385, filed Jul. 27, 2007, and 60/985,401, filed Nov. 5, 2007, both of which is incorporated by reference as if disclosed herein in its entirety.

BACKGROUND

The desire to reduce emissions of greenhouse gases to the atmosphere led to the development of carbon capture and storage (CCS) technologies that target large, point source emitters of carbon dioxide ($CO_2$). While CCS promises to have a big impact in reducing carbon emissions, even when fully deployed, CCS generally only captures about 50% of current $CO_2$ emissions. The remainder originates from small, dispersed, and mobile sources. In turn, the majority (65%) of these are associated with the transportation sector, which is also experiencing the largest growth in emissions. Emissions could also rise if the amount of oil from unconventional sources, such as tar sands, increases dramatically. Proposed solutions to effectively de-carbonize the sector include electricity and hydrogen ($H_2$) as likely candidates.

De-carbonizing transportation fuels reduce anthropogenic $CO_2$ emissions only if the source of the fuel and the overall production process is carbon neutral. For hydrogen and electricity, the key development is either the full deployment of conventional CCS or a paradigm shift to an electricity grid completely dominated by renewable power systems such as wind, solar, and biomass. Even with these developments, both CCS and renewable power have associated fugitive emissions. The $CO_2$ profile of CCS (40-152 g $CO_2$/kWh) is on a similar scale to renewable systems (12-63 g $CO_2$/kWh). Non-hydro renewable power accounts for 18% of current electricity generation, including nuclear.

The introduction of the necessary changes to the energy infrastructure, either CCS or renewable power, will take time. For example, the de-carbonized solutions also depend on the separate development of infrastructure to transport and deliver the hydrogen or electricity. As a result, "bridge" fuels, e.g., synthetic fuels having a lesser carbon footprint than current fuels, may be necessary to reduce emissions until the energy infrastructure is changed.

Much effort is being spent on developing a sustainable transportation fuel. The exact definition of sustainable generally assumes no fossil $CO_2$ emissions to the atmosphere and reduced emission of category pollutants such as sulfur compounds. An often sited fuel is hydrogen ($H_2$), which produces only water vapor upon combustion. An equally important consideration is how the hydrogen is produced. If it is produced using fossil fuels, currently by stripping natural gas, the fuel will have a fossil $CO_2$ burden. The exact burden will depend on the type of fuel, coal or natural gas, and the management plan, geological sequestration or other. It is unclear how much extra energy will be required to for transportation, handling, and on board use of hydrogen. Ethanol from biomass is also a renewable fuel option but it is unclear at this time how significant are the reductions in fossil fuels.

SUMMARY

Methods for producing a synthetic fuel are disclosed. In some embodiments, the methods include the following: thermally reforming methane and carbon dioxide to generate a syngas including a first quantity of carbon monoxide and a first quantity of hydrogen; oxidizing the quantity of first carbon monoxide with a metal to produce metal oxide and carbon thereby separating oxygen from the carbon monoxide; gasifying the carbon using steam to produce a second quantity of carbon monoxide and a second quantity of hydrogen; reacting the metal oxide with methane to produce metal oxide, carbon dioxide, and a third quantity of hydrogen; and synthesizing the first quantity of carbon monoxide, the first quantity of hydrogen, the second quantity of hydrogen, and the third quantity of hydrogen to form the synthetic fuel.

Systems for producing a synthetic fuel are disclosed. In some embodiments, the systems include the following: a reformer reactor for thermally reforming methane with carbon dioxide to produce a first quantity of carbon monoxide and a first quantity of hydrogen; an oxidation/reduction reactor for oxidizing the quantity of first carbon monoxide with a metal to produce metal oxide and carbon thereby separating oxygen from the carbon monoxide, the for gasifying the carbon using steam to produce a second quantity of carbon monoxide and a second quantity of hydrogen, and for reacting the metal oxide with methane to produce metal oxide, carbon dioxide, and a third quantity of hydrogen; a carbon dioxide capture module for capturing the carbon dioxide produced by the oxidation/reaction reactor; and a synthesis reactor for synthesizing the first quantity of carbon monoxide, the first quantity of hydrogen, the second quantity of hydrogen, and the third quantity of hydrogen to form the synthetic fuel.

Methods for producing methanol are disclosed. In some embodiments, the methods include the following: thermally reforming methane with carbon dioxide to produce a first quantity of carbon monoxide and a first quantity of hydrogen gas; oxidizing the quantity of first carbon monoxide with a metal to produce metal oxide and carbon thereby separating oxygen from the carbon monoxide; gasifying the carbon using steam to produce a second quantity of carbon monoxide and a second quantity of hydrogen gas; reacting the metal oxide with methane to produce metal oxide, carbon dioxide, and a third quantity of hydrogen gas; and synthesizing the first quantity of carbon monoxide and the first, second, and third quantities of hydrogen gas to form methanol.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1:
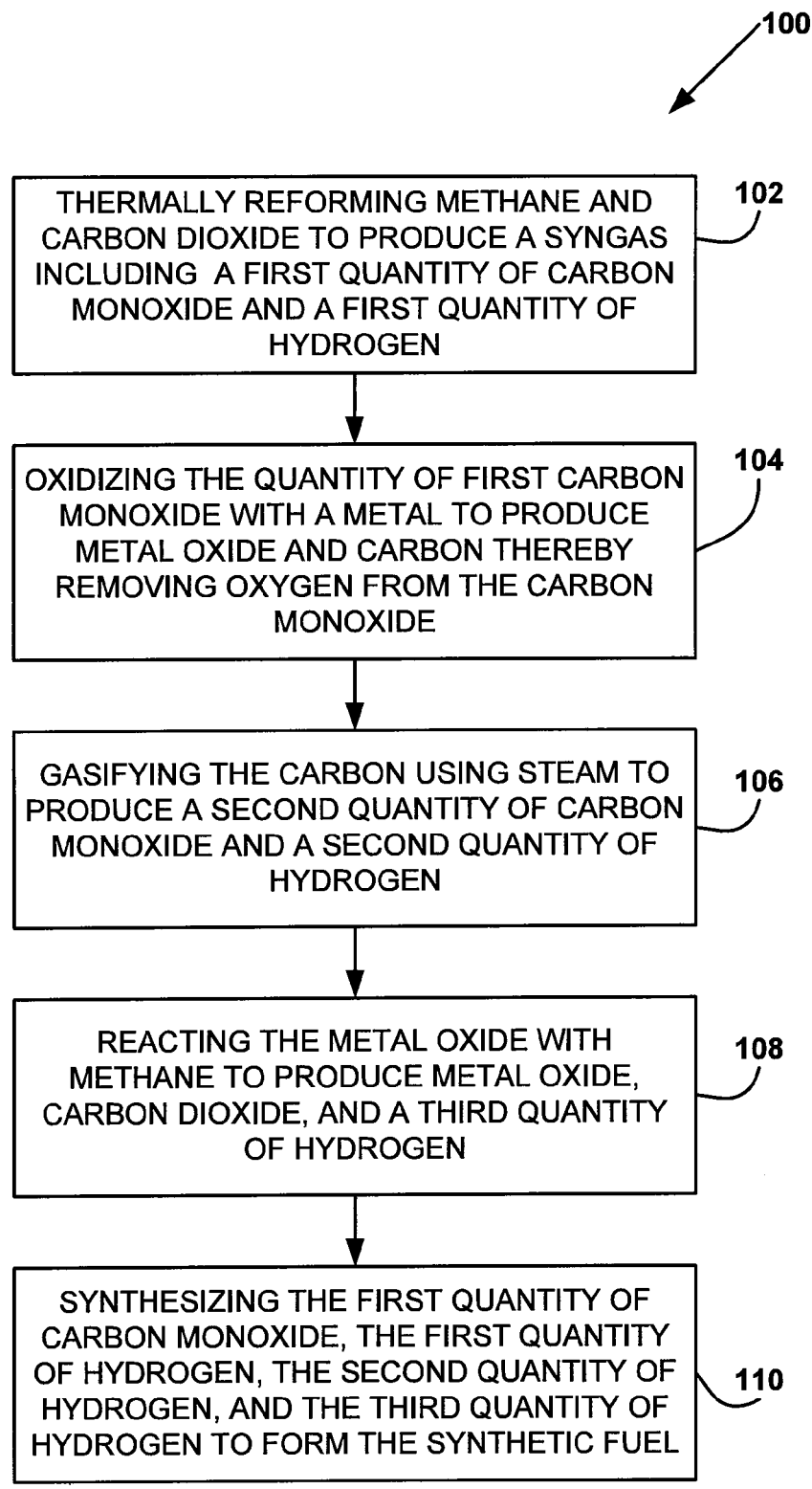
FIG. 1 is a diagram of a method according to some embodiments of the disclosed subject matter.
Figure 2:
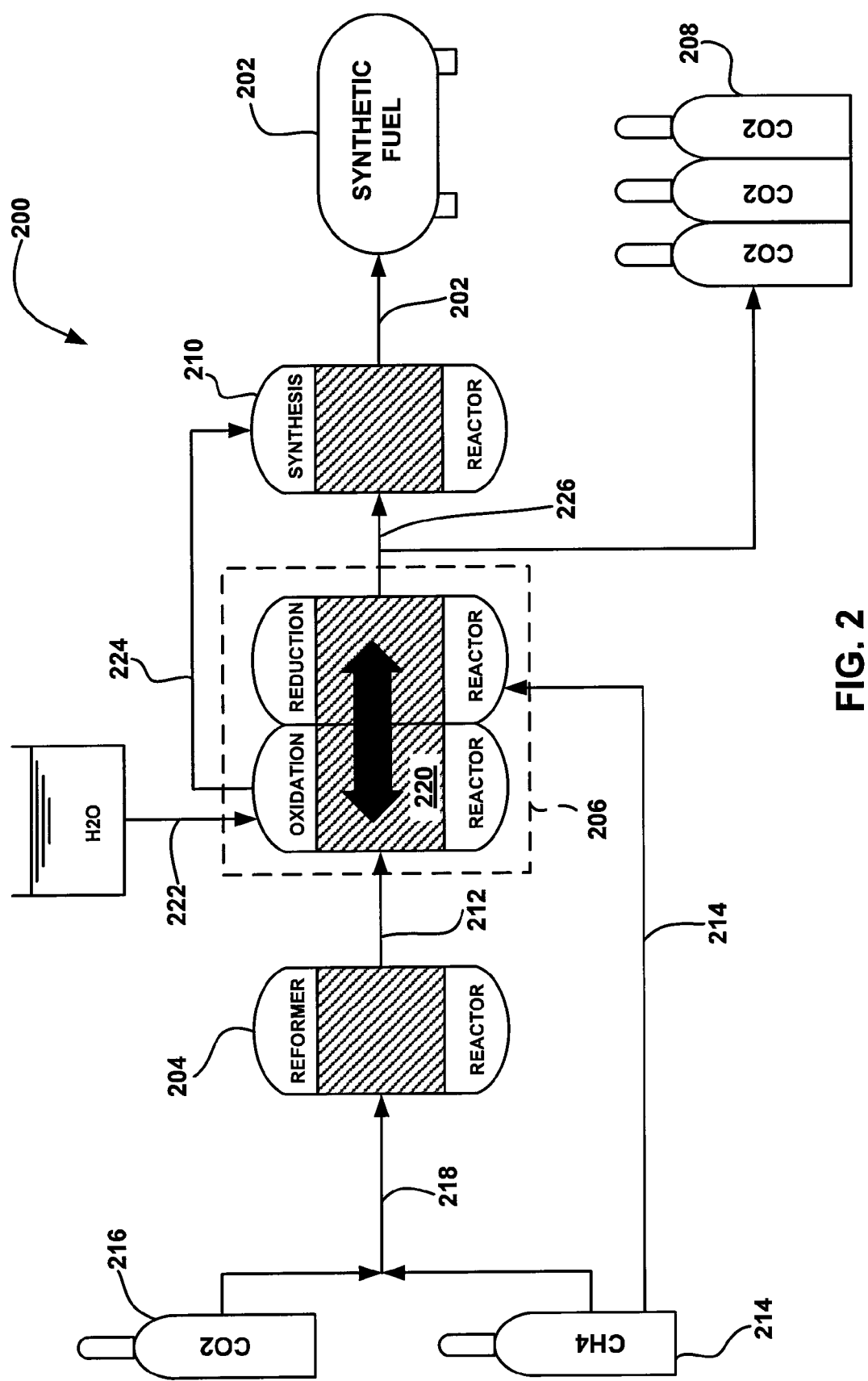
FIG. 2 is a schematic diagram of a system according to some embodiments of the disclosed subject matter.

Generally, the disclosed subject matter relates to methods and systems for producing a synthetic fuel, which include the use of chemical looping combustion (CLC) processes to condition intermediate gases formed during production of the fuel. As shown in FIGS. 1 and 2, methods and systems according to the disclosed subject matter include the reformation of methane with carbon dioxide to produce a syngas containing base ingredients for a target synthetic fuel. CLC processes are used to remove oxygen and add hydrogen to the syngas depending on the requirements of the target synthetic fuel.

Referring now to FIG. 1, some embodiments include a method 100 of producing a synthetic fuel. At 102, methane ($CH_4$) and carbon dioxide ($CO_2$) are thermally reformed according to reaction (1) to form a syngas including a first quantity of carbon monoxide (CO) and a first quantity of hydrogen ($H_2$):

$$CH_4 + CO_2 \leftrightarrow 2CO + 2H_2 \quad (1)$$

The methane used to form the syngas can be obtained from at least one of the following: a stranded natural gas well; a biogas produced from anaerobic digestion; and a combination of one or more thereof. The carbon dioxide used to form the syngas can be obtained from at least one of the following: a biogas produced from anaerobic digestion; natural gas fields with high carbon dioxide contents; carbon dioxide captured from atmospheric air; and a combination of one or more thereof. As shown in reaction (1), the syngas formed during method 100 typically includes equal moles of carbon dioxide and methane.

As mentioned above, the syngas produced by the thermal reforming of carbon dioxide and methane includes carbon dioxide and hydrogen, which will be used as the base ingredients to produce a target synthetic fuel. A variety of target synthetic fuels are presented in Table 1. The final three columns represent the difference between the reactants, which are contained in the syngas and the products, which are contained in the target synthetic fuel. A positive sign indicates an excess product while a negative sign indicates a deficient reactant.

TABLE 1

Potential Synthetic Fuels

| Fuel | Formula | C | $H_2$ | $O_2$ |
|---|---|---|---|---|
| 2xMethanol | $2(CH_4O)$ | 0 | −2 | 0 |
| Ethylene | $C_2H_4$ | 0 | 0 | +1 |
| Ethanol | $C_2H_6O$ | 0 | −1 | +0.5 |
| Butanol* | $C_4H_{10}O$ | 0 | −1 | +1.5 |

*The feedstock is double ($2CO_2 + 2CH_4$)

The relative ease of producing the synthetic fuels in Table 1 can be gauged by comparing the ratios of carbon, hydrogen, and oxygen with those present in the syngas mixture. In molar terms, reaction (1) produces two moles of carbon (C) and one mole of oxygen ($O_2$) with two moles of hydrogen ($H_2$). A comparison of this mixture with the stoichiometric equivalent in the target synthetic fuel helps ascertain the amount of gas conditioning required. For example, two moles of methanol contain two moles of C, one mole of $O_2$, and four moles of $H_2$. If the target synthetic fuel is methanol, the synthetic gas must be conditioned so that two moles of $H_2$ are added to the process to produce a stoichiometric mixture suitable for methanol synthesis.

As mentioned above, in method 100, CLC processes are used to condition the syngas so that the stoichiometry of the feed stream is adjusted according to the target synthetic fuel prior to beginning the synthesis reaction for forming the fuel. Still referring to FIG. 1, at 104, the CLC processes for conditioning begin by first oxidizing the quantity of first carbon monoxide with a metal to separate oxygen from the carbon monoxide and produce metal oxide and carbon. Then, at 106, the carbon is gasified using steam or hydrogen to produce a second quantity of carbon monoxide and a second quantity of hydrogen. At 108, the metal oxide is reacted with methane to produce metal oxide, carbon dioxide, and a third quantity of hydrogen. At 110, the first quantity of carbon monoxide, the first quantity of hydrogen, the second quantity of hydrogen, and the third quantity of hydrogen are synthesized to form the target synthetic fuel. As mentioned above, in some embodiments, the target synthetic fuel is at least one of methanol ($CH_4O$), ethylene ($C_2H_4$), ethanol ($C_2H_6O$), and butanol ($C_4H_{10}O$).

CLC technology was originally developed as a method for carbon dioxide capture in the power industry. The CLC process begins with the thermal reforming of methane and carbon dioxide followed by the conditioning of the feed mixture, i.e., syngas, to match the stoichiometry required for the target synthetic fuel. A metal oxide removes oxygen from the syngas by reducing carbon monoxide and produces hydrogen when it is reduced by methane. Between the two reactions, steam or hydrogen is used to gasify the carbon (soot) deposited during the reduction of the syngas.

In CLC, a metal oxide (MeO) is used as an oxygen carrier to transfer oxygen from air to the fossil fuel while avoiding the mixing of carbon dioxide ($CO_2$) and nitrogen ($N_2$). The reaction pair is shown schematically in reactions (2) and (3). CLC processes allow for the generation of a stream of $CO_2$ that does not contain nitrogen and is therefore easier to purify.

$$Me + Air \leftrightarrow MeO + O_2 \text{ depleted Air (oxidation)} \quad (2)$$

$$MeO + Fuel \leftrightarrow Me + CO_2 + H_2O \text{ (reduction)} \quad (3)$$

In some embodiments of the disclosed subject matter, modified CLC processes are used to remove/separate oxygen from carbon monoxide (CO) in the oxidation reaction and produce hydrogen ($H_2$) in the reduction reaction using methane ($CH_4$). The modified CLC processes according to the disclosed subject matter are shown schematically in reactions 4 and 5.

$$Me + CO \leftrightarrow MeO + C \text{ (oxidation)} \quad (4)$$

$$2MeO + CH_4 \leftrightarrow Me + CO_2 + 2H_2 \text{ (reduction)} \quad (5)$$

The used of modified CLC processes to condition the syngas allows for the optimization of the carbon monoxide (CO) to hydrogen ($H_2$) ratio preferred for fuel synthesis.

In some embodiments, the metal used in the modified CLC processes is either ferrous oxide (FeO) or ferrous ferric oxide ($Fe_3O_4$). In still other embodiments, the metal used in the modified CLC processes is mechanically milled to a particle size of less than 10 μm. Considering iron, there are three possible oxidation reactions shown sequentially as reactions 6 though 8. Each reaction results in the reduction of one mole of carbon monoxide (CO) and the production of one mole of carbon (C).

$$2Fe_3O_4 + CO_{(g)} \leftrightarrow 3Fe_2O_3 + C \quad (6)$$

$$3FeO + CO_{(g)} \leftrightarrow 4Fe_3O_4 + C \quad (7)$$

$$2FeO + CO_{(g)} \leftrightarrow Fe_2O_3 + C \quad (8)$$

The products of the reduction reactions are solid and it is generally necessary to separate the carbon for use in the synthesis reaction. One method for such a separation process is gasification using steam according to reaction 9.

$$C + H_2O_{(g)} \leftrightarrow CO_{(g)} + H_{2(g)} \quad (9)$$

The inclusion of the steam gasification results in the addition of one mole of hydrogen ($H_2$) through thermal means. The second mole of hydrogen ($H_2$) is produced in the reduction reactions for the iron compounds. The reactions 10 through 12 are the complementary reduction reactions to reactions 6 though 8. The reduction reactions are balanced to produce a mixture of carbon dioxide ($CO_2$) and hydrogen ($H_2$). In this manner, the second mole of hydrogen ($H_2$) is produced for synthesis.

  (10)

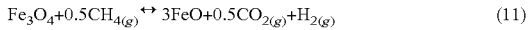  (11)

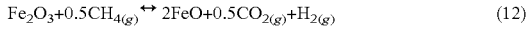  (12)

Referring now to FIG. 2, other embodiments of the disclosed subject matter include a system 200 for producing a synthetic fuel 202. System 200 generally includes connected reactors, which include a reformer reactor 204, an oxidation/reduction reactor 206, a carbon dioxide capture module 208, and a synthesis reactor 210.

Reformer reactor 204 is used to thermally reforming methane with carbon dioxide to produce a syngas 212 that contains a first quantity of carbon monoxide and a first quantity of hydrogen. A methane source 214 and a carbon dioxide source 216 are typically introduced to reformer reactor 204 via a pipe, hose, or other conduit 218.

Oxidation/reduction reactor 206 is used to contain the CLC processes. First, oxidation/reduction reactor 206 is used for oxidizing the quantity of first carbon monoxide contained in syngas 212 with a metal 220 to produce metal oxide and carbon thereby separating oxygen from the carbon monoxide. The carbon formed during oxidation of syngas 212 is gasified using steam 222 to form a stream 224 including a second quantity of carbon monoxide and a second quantity of hydrogen. Stream 224 can be directed to synthesis reactor 210 for use in the synthesis reaction. The oxidation/reduction reactor 206 is used for reacting the metal oxide with methane 214 to produce a stream 226 including metal oxide, carbon dioxide, and a third quantity of hydrogen.

Carbon dioxide capture module 208 is used to capture and store the carbon dioxide produced by oxidation/reaction reactor 206. Known CCS technologies can be used.

Synthesis reactor 210 is used for synthesizing stream 226, which includes the first quantity of carbon monoxide, the first quantity of hydrogen, the second quantity of hydrogen, and the third quantity of hydrogen, to form synthetic fuel 202.

Current methanol production is dominated by the steam reforming of methane (SRM), accounting for 75% of global production. As SRM is endothermic (224 kJ/mol), it is usually combined with auto-thermal reforming of methane where the gas is partially oxidized using oxygen and the heat released drives the SRM reaction. Conventional stream reforming using methane as fuel has a thermal efficiency of 63.6%. A lifecycle analysis of methanol production via SRM suggests that 1.16 moles of carbon dioxide ($CO_2$) are produced for every mole of methanol. Methods and systems and according to the disclosed subject matter provide advantages and benefits over known methods and systems in that depending on the feed source for methane and carbon dioxide and whether CCS technologies are employed, the emissions profile is lower than known methods and systems. For example, where biogas is used as the feed source for methane and carbon dioxide, 0.475 to 0.645 moles of carbon dioxide ($CO_2$) were generated for every mole of methanol produced, which is lower than SRM. If CCS technologies are employed, the emissions profile can be reduced and/or other feed sources can be utilized while still operating at a lower emissions profile than SRM and other known technologies.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of producing a synthetic fuel, said method comprising:
    thermally reforming methane and carbon dioxide to generate a syngas including a first quantity of carbon monoxide and a first quantity of hydrogen;
    oxidizing a first portion of said quantity of first carbon monoxide with a metal to produce metal oxide and carbon thereby separating oxygen from said carbon monoxide;
    gasifying said carbon using steam to produce a second quantity of carbon monoxide and a second quantity of hydrogen;
    reacting said metal oxide with methane to produce metal oxide, carbon dioxide, and a third quantity of hydrogen; and
    synthesizing a second portion of said first quantity of carbon monoxide, said first quantity of hydrogen, said second quantity of hydrogen, and said third quantity of hydrogen to form said synthetic fuel;
    wherein said synthetic fuel includes at least one of methanol ($CH_4O$), ethylene ($C_2H_4$), ethanol ($C_2H_6O$), and butanol ($C_4H_{10}O$).

2. The method of claim 1, further comprising:
    wherein said carbon dioxide used to generate said syngas is from at least one of a biogas produced from anaerobic digestion, natural gas fields, carbon dioxide captured from atmospheric air, and a combination of one or more thereof.

3. The method of claim 1, further comprising:
    wherein said methane used to generate said syngas is from at least one of methane contained in a stranded natural gas well, a biogas produced from anaerobic digestion, and a combination of one or more thereof.

4. The method of claim 1, wherein said metal is ferrous oxide (FeO) or ferrous ferric oxide ($Fe_3O_4$).

5. The method of claim 3, wherein said metal is mechanically milled to a particle size of less than 10 μm.

6. The method of claim 1, wherein said syngas includes equal moles of carbon dioxide and methane.

* * * * *